(12) United States Patent
Wong et al.

(10) Patent No.: US 7,856,948 B2
(45) Date of Patent: Dec. 28, 2010

(54) SELF-STEAMING COMPOSITIONS, ARTICLES COMPRISING SUCH COMPOSITIONS AND METHODS OF PREPARING SUCH COMPOSITIONS

(75) Inventors: Vincet York-Leung Wong, Hamilton, OH (US); Kenneth John Edelman, Wyoming, OH (US); Donald Louis Horning, Greensberg, IN (US); Robert Henry Rohrbaugh, Hamilton, OH (US); Brian Joseph Roselle, Fairfield, OH (US)

(73) Assignee: Wyeth LLC, Madison, NJ (US)

( * ) Notice: Subject to any disclaimer, the term of this patent is extended or adjusted under 35 U.S.C. 154(b) by 1336 days.

(21) Appl. No.: 11/070,764

(22) Filed: Mar. 2, 2005

(65) Prior Publication Data

US 2005/0262757 A1 Dec. 1, 2005

Related U.S. Application Data

(60) Provisional application No. 60/574,809, filed on May 27, 2004.

(51) Int. Cl.
C09K 5/04 (2006.01)
C06B 33/00 (2006.01)
F26B 21/08 (2006.01)
A61F 7/00 (2006.01)

(52) U.S. Cl. .......................... 122/211; 44/250; 44/251; 34/210; 607/114; 252/76; 252/8.91; 252/67; 252/183.13

(58) Field of Classification Search .................. 44/250, 44/251; 252/76, 183.13, 8.91, 67; 34/210; 607/114; 122/211
See application file for complete search history.

(56) References Cited

U.S. PATENT DOCUMENTS

| | | | |
|---|---|---|---|
| 2,243,110 A | 12/1935 | Madaras | |
| 2,793,946 A | 5/1957 | Paschal | |
| 2,807,535 A | 9/1957 | Segre | |
| 2,900,247 A | 8/1959 | Celada | |
| 2,915,379 A | 12/1959 | Agarwal | |
| 3,128,174 A | 4/1964 | Celada | |
| 3,136,623 A | 6/1964 | Mader et al. | |
| 3,136,624 A | 6/1964 | Mader et al. | |
| 3,136,625 A | 6/1964 | Mader et al. | |
| 3,301,250 A | 1/1967 | Glasser | |
| 3,375,098 A | 3/1968 | Marshall | |
| 3,423,201 A | 1/1969 | Celada | |
| 3,684,486 A | 8/1972 | Osman | |
| 3,765,872 A | 10/1973 | Celada | |
| 3,770,421 A | 11/1973 | Celada | |
| 3,779,741 A | 12/1973 | Celada | |
| 3,816,102 A | 6/1974 | Celada | |
| 3,827,879 A | 8/1974 | Mac et al. | |
| 3,890,142 A | 6/1975 | Celada | |
| 3,904,397 A | 9/1975 | Celada | |
| 4,145,184 A | 3/1979 | Brain et al. | |
| 4,152,272 A | 5/1979 | Young | |
| 4,209,417 A | 6/1980 | Whyte | |
| 4,515,705 A | 5/1985 | Moeddel | |
| 4,649,895 A | 3/1987 | Yasuki et al. | |
| 5,046,479 A | 9/1991 | Usui | |
| 5,233,981 A | 8/1993 | Miyashita | |
| 5,342,412 A | 8/1994 | Usui | |
| 5,366,492 A | 11/1994 | Usui | |
| 5,662,624 A | 9/1997 | Sundstrom et al. | |
| 5,918,590 A | 7/1999 | Burkett et al. | |
| 5,984,995 A | 11/1999 | White | |
| 6,020,040 A | 2/2000 | Cramer et al. | |
| 6,099,556 A | 8/2000 | Usui | |
| 6,158,427 A | 12/2000 | McGuire et al. | |
| 6,409,746 B1 * | 6/2002 | Igaki et al. ................... 607/109 |
| 6,436,126 B1 | 8/2002 | McAfee | |
| 6,629,964 B1 | 10/2003 | Ono et al. | |
| 6,666,836 B1 | 12/2003 | Islava | |
| 2001/0042546 A1 * | 11/2001 | Umeda et al. .......... 128/206.21 |
| 2002/0020406 A1 | 2/2002 | Minami | |
| 2004/0042965 A1 | 3/2004 | Usui et al. | |
| 2004/0178384 A1 | 9/2004 | Usui | |
| 2004/0217325 A1 * | 11/2004 | Usui et al. .................... 252/70 |

FOREIGN PATENT DOCUMENTS

| | | |
|---|---|---|
| EP | 0286421 | 4/1986 |
| EP | 1181911 A1 | 8/2001 |
| EP | 1577363 A1 | 12/2003 |
| GB | 2205496 A | 6/1988 |
| WO | WO 97/01313 | 1/1997 |
| WO | WO 97/33542 | 9/1997 |
| WO | WO 97/36968 | 10/1997 |
| WO | WO 98/29066 | 7/1998 |
| WO | WO 03097764 A1 * | 11/2003 |

* cited by examiner

Primary Examiner—Ellen M McAvoy
Assistant Examiner—Pamela Weiss
(74) Attorney, Agent, or Firm—Joel Silver; Jeffrey M. Gold

(57) ABSTRACT

Disclosed herein are compositions which are exothermic upon contact with oxygen and are self-steaming. The various described embodiments include compositions comprising:
 (a) a fuel component;
 (b) a water manager component; and
 (c) water.

In one embodiment, the water manager component, has a mean particle size distribution of greater than about 250 microns.

Alternatively or additionally, the ratio of the water manager component to the water is from about 0.001:1 to about 0.2:1, by weight.

Alternatively or additionally, the fuel component comprises sponge iron.

Alternatively or additionally, the composition comprises a volatile component.

In yet another embodiment, articles comprising the compositions are described. Further, methods of making the compositions are described.

35 Claims, No Drawings

SELF-STEAMING COMPOSITIONS, ARTICLES COMPRISING SUCH COMPOSITIONS AND METHODS OF PREPARING SUCH COMPOSITIONS

This application claims the benefit of U.S. Provisional Application Ser. No. 60/574,809, filed on May 27, 2004.

FIELD OF THE INVENTION

The present invention is directed to compositions which are self-steaming. The compositions may be utilized in a variety of articles and for a variety of methods, including those which utilize steam generation for treating fabrics, providing health benefits, aesthetic benefits, or the like.

BACKGROUND OF THE INVENTION

Disposable thermal devices based on, for example, iron oxidation are known. However, many such devices are limited in their utility, such as for use merely to heat desired components including mammalian joint constituents, such as in the knee, elbow, and the like. While such devices deliver desired and controlled heat, it would be advantageous to expand the utility of such devices, such to capitalize upon the unique capability of heat generation without need for an external energy source.

The present invention advances the utility of exothermic compositions by providing means for self-steaming which is in addition to the exothermic character of such composition. However, as could be imagined, it is difficult to practically deliver such compositions, given the inherent need for retaining water in or around the exothermic composition without problematic flooding. The invention herein overcomes such obstacle by providing portable and/or disposable compositions and articles which are used as a source of steam and heat, through use of a water manager component, which advantageously holds moisture within the present compositions and articles, allowing for later release as steam when the composition or article is ready for use. Particular embodiments of the invention are herein directed as various solutions to the foregoing problems.

The invention may be utilized in a wide variety of applications. For example, it is highly advantageous to provide means for cleaning or refreshing fabrics without the need for labor-intensive pressing, or the like. In addition, the present articles may be directed to various health care applications. To illustrate, the article may be a vaporizer, such as a self-steaming vaporizer or vapor therapy humidifier. Not limited to this application, the article may serve to moisturize dry or irritated respiratory passages or relieve cough or other symptoms associated with cold. These and other benefits of the present invention are further described herein.

SUMMARY OF THE INVENTION

The present invention is directed to compositions which are exothermic upon contact with oxygen and are self-steaming.

The various embodiments of the invention include compositions comprising:
(a) a fuel component;
(b) a water manager component; and
(c) water.

In one embodiment, the water manager component, has a mean particle size distribution of greater than about 250 microns.

Alternatively or additionally, the ratio of the water manager component to the water is from about 0.001:1 to about 0.2:1, by weight.

Alternatively or additionally, the fuel component comprises sponge iron.

Alternatively or additionally, the composition comprises a volatile component.

In yet another embodiment, articles comprising the compositions are described. Further, methods of making the compositions are described.

DETAILED DESCRIPTION OF THE INVENTION

Various documents including, for example, publications and patents, are recited throughout this disclosure. All such documents are hereby incorporated by reference.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention, various embodiments and/or individual features are disclosed. As will be apparent to the ordinarily skilled practitioner, all combinations of such embodiments and features are possible and can result in preferred executions of the present invention.

The compositions herein may comprise, consist essentially of, or consist of any of the elements as described herein.

While various embodiments and individual features of the present invention have been illustrated and described, various other changes and modifications can be made without departing from the spirit and scope of the invention. As will be also be apparent, all combinations of the embodiments and features taught in the foregoing disclosure are possible and can result in preferred executions of the invention.

As used herein, the term "self-steaming" means possessing the ability to generate and release steam or vapor from water present in the referenced composition upon contact with gas comprising oxygen, such as air. In accordance with the present invention, the self-steaming compositions do not rely on the input of energy from sources separate from the self-steaming composition.

As used herein, the term "steam" means vaporized water as an invisible gas and/or the visible mist that condenses therefrom.

Compositions of the Present Invention

The present invention is directed to compositions which are exothermic upon contact with oxygen and are self-steaming. The various embodiments of the invention include compositions comprising:
(a) a fuel component;
(b) a water manager component; and
(c) water.

In one embodiment, the water manager component has a mean particle size distribution of greater than about 250 microns.

Alternatively or additionally, the ratio of the water manager component to the water is from about 0.001:1 to about 0.2:1, by weight.

Alternatively or additionally, the fuel component comprises sponge iron.

Alternatively or additionally, the composition further comprises a volatile component.

The various components of various embodiments of the compositions are described as follows:

The Fuel Component

The present compositions comprise a fuel component. As used herein, the fuel component comprises one or more materials which are self-steaming in conjunction with the remaining components of the composition (including the water manager component and water). In particular, the fuel component is the reactant for the self-steaming process upon contact with oxygen.

A variety of materials will be understood by those of ordinary skill in the art as being useful as the fuel component. See e.g., U.S. Pat. Nos. 5,918,590 and 5,984,995.

In one embodiment herein, the fuel component may comprise a material selected from the group consisting of metals, metal salts, carbon, and mixtures thereof. For example, in one embodiment, the fuel component may comprise iron, a metal salt, and activated carbon.

Metals

Metals which may be used herein will be well-known to those of ordinary skill in the art. For example, iron, aluminum, zinc, copper, lead, and the like may be utilized.

In one embodiment, the metal is iron. Iron is the anode for the electrochemical reaction involved in the exothermic oxidation of iron. Suitable sources for iron include cast iron powder, reduced iron powder, electrolytic iron powder, scrap iron powder, sponge iron, pig iron, wrought iron, steel, iron alloy, and the like, all of which shall include treated varieties of these irons. There is no particular limitation to their purity, kind, and the like, so long as it can be used to generate steam or vapor as part of the self-steaming composition.

Sponge iron is one example of the iron, which may be particularly advantageous due to the high internal surface area of this iron source. As the internal surface area is orders of magnitude greater than the external surface area, reactivity may not be controlled by particle size. Non-limiting examples of sponge iron include M-100 and F-417, commercially available from Hoeganaes Corp., N.J.

Sponge iron is a material utilized in the steel making industry as a basic source for the production of steel. Without intending to be limited by any method of production, sponge iron may be produced by exposing hematite ($Fe_2O_3$) iron ore in comminuted form to a reducing gas environment at temperatures somewhat below blast furnace temperatures. The production of sponge iron is the subject of a large number of patents, including: U.S. Pat. Nos. 2,243,110; 2,793,946; 2,807,535; 2,900,247; 2,915,379; 3,128,174; 3,136,623; 3,136,624; 3,136,625; 3,375,098; 3,423,201; 3,684,486; 3,765,872; 3,770,421; 3,779,741; 3,816,102; 3,827,879; 3,890,142; and 3,904,397.

The ordinarily skilled artisan will be able to manipulate the amount of metal present within the composition in accordance with the level of heat and/or steam desired. As an example, the compositions may comprise from about 30% to about 95%, alternatively from about 40% to about 85%, alternatively from about 50% to about 70% of the metal, by weight of the composition.

Metal Salts

Any of various metal salts may be utilized in the present compositions. The metal salt serves as a reaction promoter for activating the surface of the metal to ease the oxidation reaction with air and provides electrical conduction to the exothermic composition to sustain the corrosive reaction.

The metal salts useful in the present compositions include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of the metal. Exemplary metal salts include sodium chloride, cupric chloride, and mixtures thereof.

The ordinarily skilled artisan will be able to manipulate the amount of metal salts present within the composition in accordance with the level of heat and/or steam desired. Typically, the exothermic composition comprises from about 0.5% to about 10%, alternatively from about 1% to about 5% metal salts, all by weight of the composition.

Carbon

Carbon (including carbonaceous material) selected from the group consisting of activated carbon, non-activated carbon, and mixtures thereof may be used in the compositions herein. Activated carbon may be used as a catalyst for the reactions generated herein. Specifically, activated carbon, when wet, has the ability to adsorb oxygen. Activated carbon may also serve as the cathode for the electrochemical reaction involved in the exothermic oxidation of metal. Furthermore, activated carbon serves as a water-releasing agent as it helps facilitate the release of water due to its extremely porous inner structure, thus allowing it to temporarily retain water until the steam generation process begins. Activated carbon may also adsorb odors such as those that may be caused by the oxidation of metal.

Activated carbon prepared from coconut shell, wood, charcoal, coal, bone coal, and the like are useful, but those prepared from other raw materials such as animal products, natural gas, fats, oils and resins are also useful in the particulate exothermic composition optionally used herein. There are no limitations to the kinds of activated carbon used; for example, the preferred activated carbon has superior water holding capabilities and the different carbons may be blended to reduce cost. Therefore, mixtures of the above carbons are useful in the present invention as well.

The ordinarily skilled artisan will be able to manipulate the amount of carbon present within the composition in accordance with the level of heat and/or steam desired. For example, the composition may comprise from about 0.5% to about 25%, alternatively 1% to about 20%, alternatively from about 2% to about 15%, all by weight of the composition.

The Water Manager Component

The present compositions comprise a water manager component. As used herein, the water manager component comprises one or more materials which enable the retention of water physically or chemically within the composition, such that the composition will release the water as steam. In particular, the water manager component is the component which enables the retention of sufficient water within the composition, such that the water may later be released upon self-steaming. While not intending to be bound by theory, it is believed that the water manager component can facilitate the generation of an increased volume of steam by releasing water at a controlled rate. Furthermore, the water manager component can prevent or inhibit water from entering, or being maintained in, the interstitial voids of the various particles of the composition, thereby helping to prevent or inhibit flooding.

A variety of materials will be understood by those of ordinary skill in the art as being useful as the water manager component. See e.g., U.S. Pat. Nos. 5,918,590 and 5,984,995. For example, those having capillary function and/or hydrophilic property may be utilized. To illustrate, the composition may comprise a material selected from the group consisting of vermiculite, porous silicates, wood powder, wood flour, cotton, paper, vegetable matter, absorbent gelling material, carboxymethylcellulose salts, inorganic salts, and mixtures thereof.

As an example, an absorbent gelling material may be used. As is well-known, absorbent gelling materials are materials having fluid-absorbing properties. Such materials form hydrogels on contact with water. One type of hydrogel-forming, absorbent gelling material is based on a polyacid, for example polyacrylic acid. Hydrogel-forming polymeric materials of this type are those which, upon contact with liquids such as water, imbibe such fluids and thereby form the hydrogel. These preferred absorbent gelling materials will generally comprise substantially water-insoluble, slightly cross-linked partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, certain absorbent gelling materials include hydrolyzed acrylonitrile grafted starch, acrylic acid grafted starch, polyacrylate, maleic anhydride-based copolymer, and combinations thereof. Absorbent gelling materials may include the polyacrylates and acrylic acid grafted starch.

The ordinarily skilled artisan will be able to manipulate the amount of water manager component present within the composition in accordance with the level of steam desired. For example, the composition may comprise from about 0.1% to about 30%, alternatively from about 0.5% to about 20%, alternatively from about 1% to about 10% water manager component, all by weight of the composition.

Water

The water used herein may be from any appropriate source. For example, tap water, distilled water, or deionized water, or any mixture thereof, may be used.

The water may be incorporated directly in the form of liquid water, or water that is physically or chemically held to the separate water manager component, or any combination thereof.

The ordinarily skilled artisan will be able to manipulate the amount of water present within the composition in accordance with the level of heat and/or steam desired. When water is consumed in a reaction where heat and steam are released, an excess of water beyond the stoichiometric amount need for the reaction is necessarily added to provide a source of water used for producing steam. For example, the composition may comprise from about 1% to about 60%, alternatively from about 10% to about 30% water, all by weight of the composition.

Particle Size

In one embodiment herein, the present compositions advantageously comprise the fuel component and the water manager component, wherein the fuel component may have a first mean particle size distribution and the water manager component may have a second mean particle size distribution.

For example, it is found herein that distinct advantages relative to the art are provided wherein the water manager component has a relatively high mean particle size distribution. For example, increasing the mean particle size distribution may have advantages in terms of enhancing safety upon preparing the present compositions, as larger particle size distribution may decrease risks associated with particle inhalation and other respiratory effects.

To illustrate, in one embodiment of the invention, the water manager component (or, alternatively or additionally where explicitly specified, any individual material thereof) has a mean particle size distribution greater than about 250 microns, or at least about 400 microns, or from about 400 microns to about 800 microns. In an additional or alternative embodiment herein, the fuel component (or, alternatively or additionally where explicitly specified, any individual material thereof (e.g., iron) has a mean particle size distribution of at least about 100 microns, or from about 100 microns to about 300 microns.

As used herein, and as will be commonly understood in the art, the term "mean particle size distribution," with reference to a given component, is the mean value of the particles present in the component based on the sizes of the individual particles in the component. The mean particle size distribution of the given component may be measured using a HORIBA LA-910 laser scattering particle size distribution analyzer (Horiba, Calif.), or other instrument providing substantially similar results.

In this embodiment, the relative increase of these particle size distributions is preferred in order to minimize segregation effects. Reducing segregation effects among components allows desired thermal and/or steaming effects. In particular, minimizing segregation effects is desirable when the composition is used to make multi-cell heat packs where the cell weight is in order of 5 grams or less. Filling multi-cells with the right amount of chemistry requires a highly flow-able chemistry pre-mix composition, such as the pre-mix composition defined herein. A pre-mix composition having high flow ability would also be prone to segregation, especially if the particles differ considerably in particle size. It is known that the size difference between the water manager and fuel component can vary. The size difference can be contributed to the belief that fines (such as, for example, fine iron powder) is necessary for rapidity of reaction rate. On the other hand, the particle size of the water manager needs to be large in order to maximize water holding capacity in its inner structure (i.e. vermiculite) or to minimize respiratory dusting issues (i.e. AGM). Indeed, it is found herein that the aforementioned relatively increased mean particle size distributions reduce segregation effects among components within the composition. This allows for the high speed production of multi-cell heat packs that provide more than 8 hours of therapeutic heat and fast self steaming multi-cell heat packs. Without intending to be limited by theory, this is based on a finding that the porosity of the mixture of particles utilized may govern reaction rate, rather than (or in addition to) surface area of the metal. Thus, the multi-cell heat packs used for therapeutic heating has a high reaction efficiency (e.g., less metal or other material may be necessary) since the composition has a high level of moisture needed for the reaction, yet the high level of water added does not "flood the reaction" (Reaction fails to heat up due to the inability of oxygen to diffuse through the excess water that fills the interstitial particle voids.). Similarly, the high porosity of the chemistry composition enables self steaming multi cell heat packs to quickly heat up to steaming conditions.

Ratio of Water Manager Component to Water

In an additional or alternative embodiment herein, the ratio of water manager component to water is manipulated. Indeed, it is found herein that use of the highly efficient water manager components herein enables a decreased level of water manager component relative to the water, which is desirable for a variety of reasons, including cost-effectiveness of the composition (and therefore availability of the composition to the user). For example, in one embodiment herein, the ratio of the water manager component to the water is from about 0.001:1 to about 0.2:1, or from about 0.01:1 to about 0.17:1, or from about 0.05:1 to about 0.12:1, all by weight.

Articles of the Present Invention

The present invention is further directed to articles comprising any of the various compositions as described herein.

Any of the various compositions described herein may be associated with a substrate or other material which enables convenient use for any of a variety of applications.

For example, the present articles may be directed to various health care applications. To illustrate, the article may be a vaporizer, such as a self-steaming vaporizer or vapor therapy humidifier. Not limited to this application, the article may serve to moisturize dry or irritated respiratory passages or relieve cough or other symptoms associated with cold. As a non-limiting example, the article of the present invention may be a commercial vaporizer, such as a VICKS® Vaporizer as marketed by Kaz Corporation, New York, N.Y., except that it is adapted to contain a self-steaming (including, vaporizing) composition as described herein such that the vaporizer is portable and not dependent upon an external source of energy for operation. In this embodiment, a sub-article comprising the composition of the present invention is contained within the vaporizer article, such that upon activation the composition is self-steaming (including, self-vaporizing) for the benefit of the user.

As another example, the compositions or articles herein may be used in various fabric care applications, for example, to impart fragrance to fabrics (such as, for example, clothing, linen, draperies, clothing accessories, leather, floor coverings, tote bags, furniture covers, tarpaulins, shoes, and the like. Articles in accordance with this embodiment are described in co-pending patent application to Roselle et al., assigned to The Procter & Gamble Co., and filed on May 26, 2004.

In order to enable the various embodiments of the present articles, the articles may comprise a thermal pack. In one particular embodiment herein, the thermal packs may have at least one continuous layer of a material which preferably exhibits specific thermophysical properties, and optionally one or more (including two or more) individual heat cells which preferably comprise a composition as described herein, spaced apart and fixed within or to the structure of the thermal pack. The cells may be of a unified structure, comprising the exothermic and self-steaming composition, enclosed within two layers, wherein at least one layer may be permeable to air, capable of providing long lasting heating, and having specific physical dimensions and fill characteristics. These cells can be used as individual temperature control units, or in a thermal pack comprising a plurality of individual cells. Thermal packs have been widely disclosed in the art, such as at U.S. Pat. No. 6,020,040. Alternatively, the thermal pack is such that is contains a composition as described herein in a loose configuration, wherein the various particles of the composition may be free-flowing within the thermal pack. The thermal pack, regardless of configuration, typically comprises a material which is permeable to air, such that the composition may initiate the self-steaming process when ready for use.

By way of example, the thermal pack may be constructed as a bag or other enclosure which surrounds the composition as described herein, wherein the composition may be free-flowing within the enclosure. The thermal pack is permeable to air. The thermal pack may then be further enclosed in a device which is impermeable to air, in order to avoid exposure of the compositions to air or other source of oxygen until the article or composition is intended for use.

By way of further example, another thermal pack may be constructed by forming a pocket in a base material. The pocket is filled with a composition as described herein. After filling the pocket, a cover material is placed over the pocket and heat sealed to the base material around the periphery of the pocket, encapsulating the exothermic and self-steaming composition in the heat cell.

The heat cells can have any geometric shape, e.g., disk, triangle, square, cube, rectangle, cylinder, ellipsoid and the like, all, some, or none of which may contain a hole through the middle or other reservoir. For example, the shape may be an ellipsoid geometry. Alternatively, cells having geometric shapes other than an ellipsoid shape, such as a disk shape may be used.

The ordinarily skilled artisan will understand that, wherein a given thermal pack comprises a plurality of heat cells, the heat cells may be of various shapes or sizes and therefore need not (but may be) uniform.

Oxygen permeability, allowing enhancement of the exothermic and self-steaming reaction, may optionally be provided by selecting materials for the article that have the specifically desired permeability properties. It is particularly useful to utilize materials as part of the article which enable relatively high oxygen permeability for use with the self-steaming materials herein. The desired permeability properties may be provided by inherently porous films or by films which have pores or holes formed therein. The formation of these holes/pores may be via extrusion cast/vacuum formation or by hot needle aperturing.

For example, oxygen permeability of at least about 10 $ft^3$/min, alternatively at least about 20 $ft^3$/min, alternatively at least about 70 $ft^3$/min, all measured in accordance with the following method, wherein maximum oxygen permeability is only optionally limited by ability of the referenced material to inhibit the self-steaming composition from flowing through the aperture. As a further example, the oxygen permeability may be from about 10 $ft^3$/min to about 400 $ft^3$/min, alternatively from about 20 $ft^3$/min to about 150 $ft^3$/min, alternatively from about 70 $ft^3$/min to about 130 $ft^3$/min, all measured in accordance with the following method. Oxygen permeability is measured utilizing a TexTest FX3300 instrument, commercially available from TexTest AG, Switzerland. The instrument is fitted with a 38 $cm^2$ test head. The permeability of a given material is measured, with a test pressure set at 125 Pa, in accordance with the manufacturer specifications, generally as follows: the material for measurement is placed over the vacuum port and under the test head of the instrument, minimizing any wrinkles in the material to the extent feasible. The test is commenced by pressing on the test head claming lever, engaging the vacuum. The instrument reaches equilibrium, and then the displayed value is recorded.

The velocity, duration, and temperature of the thermogenic oxidation reaction of the exothermic, self-steaming composition can be, in part, controlled as desired by changing the area of contact with air, more specifically, by changing the oxygen diffusion/permeability. Other methods of modifying reaction include choice of component within the composition, for example, by choosing sponge iron, modifying particulate size, or the like as described herein above.

Oxygen permeable materials may be made from any number of different materials. For example, such materials may include, but are not limited to, woven and knit fabrics, nonwovens (e.g., spunbound nonwoven or carded nonwovens), and the like. For example, a suitable nonwoven is available from PGI (Polymer Group International) of Waynesboro, Va., as material number W502FWH.

One or more oxygen impermeable materials may also be utilized to construct the thermal pack. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, preferably extruded, more preferably coextruded, most preferably coextruded with a low melt temperature polymer including, but not limited to, ethylene vinyl acetate copolymer, low density polyethylene, and mixtures thereof.

For example, the material may comprise polypropylene, such as a coextruded material comprising polypropylene. For example, a suitable heat-sealable film is a polypropylene/ ethylene vinyl acetate (PP/EVA) film available from Clopay Plastics of Cincinnati, Ohio, as material number DH245.

Attachment of the various materials of the articles described herein may be achieved by any number of attachment means known in the art. These include, but are not limited to, hot melt adhesive including spiral sprays, meltblown, control coat, and the like, latex adhesives applied via spray, printing, gravure, and the like, thermal bonding, ultrasonic, pressure bonding, and the like. For example, an adhesive layer may be used. One particular method includes a hot melt adhesive available as 70-4589 from National Starch and Chemical Co., Bridgewater, N.J., applied via a hot melt system.

The present compositions are exothermic upon contact with oxygen and are self-steaming. As such, it may be important to avoid exposure of the compositions to air or other source of oxygen until the composition is intended for use. In one embodiment of the present invention, articles comprising any of the various compositions described herein and a secondary enclosure which contains the composition, wherein the enclosure is impermeable to air, are further provided. See e.g., U.S. Pat. No. 4,649,895. Alternatively or additionally, other means may also be used to prevent an oxidation reaction from occurring before desired, such as oxygen-impermeable removable adhesive strips placed over the aeration holes such that, when the strips are removed, oxygen is allowed to enter the cells, thus activating the oxidation reaction.

For example, in one non-limiting embodiment, the self-steaming composition may be activated as follows: The article comprising the composition may include an oxygen impermeable plastic overwrap. A tear-tab or notch may be included on the overwrap for easy access by a user. Instructions may be included with the enclosure instructing a user to tear open the overwrap to remove the article comprising the self-steaming composition. This opening action immediately mixes proximal oxygen contained in the ambient air with the composition to initiate the self-steaming process.

For practicality, the self-steaming process is typically designed in such a way that the steaming occurs at the desired time. As such, the composition is generally contained or presented in a manner such that the steaming can be started or activated as needed. For example, the present self-steaming compositions may be contained within an enclosure which is impermeable to air, wherein steaming may be started or activated through disruption of the enclosure.

As an additional or alternate example, for compositions that react to form steam, there may be a barrier between reactive components to prevent the reaction from occurring until desired. In this optional embodiment, the activation of the composition may be achieved by a removal or disruption of a barrier which allows the composition to interact in a manner that will create the desired self-steaming effect.

Upon activation, the self-steaming composition may generate at least about $2 \times 10^{-5}$, or at least about $5 \times 10^{-5}$ grams/minute of steam.

The Volatile Component

In one embodiment herein, the compositions or articles may comprise a volatile component. The volatile component comprises one or more of any materials which are volatile, at ambient pressure, at temperatures greater than about 25° C., or greater than about 30° C., or greater than about 34° C., or greater than about 39° C., or greater than about 42° C. The volatile component may include perfumes, silicones, essential oils and aromatic oils; these are of course well-known in the art.

For example, the present compositions or articles herein may be used in various health care applications. To illustrate, the article may be a self-steaming vaporizer. Not limited to these applications, the volatile component of the composition used in such article may comprise, for example, one or more materials which serve to moisturize dry or irritated respiratory passages or relieve cough or other symptoms associated with cough and cold. Non-limiting examples of such materials include essential oils and other materials, including camphor, menthol, eucalyptus, peppermint, spearmint, methyl salicylate, bornyl acetate, lavender, ephedrine, angelica root, aniseed, basil, bay, bergamot, cajeput, cardamom, cassia, cedarwood, chamomile, sage, clove, cinnamon, coriander, cumin, fennel, frankincense, geranium, ho-wood, lemongrass, lemon, litsea, majoram, melissa, myrrh, myrtle, niaouli, neroli, nutmeg, orange, palmarosa, patchouli, pimento berry, pine needle, ravensara aromatica, rosewood, rosemary, tea tree, thyme, verbena, mixtures thereof, and the like. The preferred volatile components for use in the present invention include eucalyptus, camphor, menthol, and mixtures thereof.

As another example, the compositions or articles herein may be used in various fabric care applications, for example, to impart fragrance to fabrics (such as, for example, clothing, linen, draperies, clothing accessories, leather, floor coverings, tote bags, furniture covers, tarpaulins, shoes, and the like. Not limited to these applications, the volatile component may comprise, for example, one or more perfumes.

Perfumes are widely known in the art and, of course, conventional perfumes may be utilized. Selection of the perfume used herein may be based upon the desired fragrance characteristics imparted by the composition or article upon self-steaming.

Non-limiting perfumes include those described in U.S. Pat. Nos. 4,145,184; 4,209,417; 4,515,705; and 4,152,272. Additionally, many perfumes, along with their odor and/or flavor characters, and their physical and chemical properties, such as boiling point and molecular weight, are disclosed in "Perfume and Flavor Chemicals (Aroma Chemicals)," Steffen Arctander (1969).

Moreover, further non-limiting examples of perfumes include: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxy-citronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Other non-limiting examples include amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiary-butyl-alpha-methyl hydrocinnamic aldehyde), gamma-methyl ionone, nerolidol, patchouli alcohol, phenyl hexanol, beta-selicarb, trichloromethyl phenyl carbinyl acetate, triethyl citrate, vanillin, and veratraldehyde. Cedarwood terpenes are composed mainly of alpha-cedrene, beta-cedrene, and other sesquiterpenes.

Other non-limiting examples include benzophenone, benzyl salicylate, ethylene brassylate, galaxolide (1,3,4,6,7,8-hexahydro-4,6,6,7,8,8-hexamethyl-cyclopenta-gamma-2-benzopyran) hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

The volatile component can be delivered by direct volatilization of the component by the steam generated. In this case, the volatile component is incorporated directly within the self-steaming composition or alternatively in or on a substrate or other material of the article, wherein the steam is in thermal communication with the material so as to release the volatile component from the material. Non-limiting examples include wherein a perfume is incorporated directly in the self-steaming composition or alternately wherein a perfume is impregnated onto a material (for example, a non-woven substrate or a fabric softening sheet (such as BOUNCE, commercially available from The Procter & Gamble Co., Cincinnati, Ohio) that is in thermal communication with the self-steaming composition. The steam volatilizes the perfume such that the perfume is carried away along with the steam.

The volatile component may also be delivered in the form of an azeotrope. As the steam is formed from water, a consistent mix of water and volatile component can be volatilized off in the form of an azeotrope.

Other Optional Components

Other optional components of the present compositions or articles herein may include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium thiosulfate, sodium sulfite, sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and alpha-starch, and surfactants such as those included within the anionic, cationic, nonionic, zwitterionic, and amphoteric types. Still other optional components may be included within the compositions or articles herein, as appropriate, including extending agents such as metasilicates, zirconium, and ceramics. Other optional components herein include one or more benefit agents. Where present, the benefit agent selected will be dependent upon the intended use of the composition or article of the present invention.

For example, the compositions or articles herein may be used to self-steam fabrics (such as, for example, clothing, linen, draperies, clothing accessories, leather, floor coverings, tote bags, furniture covers, tarpaulins, shoes, and the like. In such an instance, the benefit agent may include, for example, one or more softening agents, crispening agents, water and/or stain repellents, refreshing agents, antistatic agents, antimicrobial agents, durable press agents, wrinkle resistant agents, wrinkle release agents, odor resistance agents, abrasion resistance agents, solvents, and mixtures thereof. Non-limiting examples of benefit agents include silicone, starch, wrinkle-releasing agent, perfume, surfactants, preservatives, bleaches, auxiliary cleaning agents, fabric shrinkage reducing compositions, organic solvents and mixtures thereof. Non-limiting examples of organic solvents include glycol ethers, specifically, methoxy propoxy propanol, ethoxy propoxy propanol, propoxy propoxy propanol, butoxy propoxy propanol, butoxy propanol, ethanol, isopropanol and mixtures thereof.

The compositions or articles of the present invention may also include one or more other optional signal components, a non-limiting example of which is a component that enables communication of the status of the self-steaming process or condition of the composition or article to a user. For example, the compositions or articles may enable a signal which indicates when steaming has commenced and/or concluded. Non-limiting examples of signals which may be enabled include color, sound, and/or olfactory signals.

One non-limiting example of such a signal component includes a color-changing dye or paint that is sensitive to changes in temperature or humidity. An example of a suitable color changing paint is KROMAGEN 75 manufactured by TMC U.S.A. of Glenview, Ill. As an example, wherein the signal component is included, the may comprise from about 0% to about 20% of the signal component, by weight of the composition or article.

Methods of Production

The various components of the self-steaming compositions and articles herein may be blended together in accordance with any number of various processes. For example, when utilizing a self-steaming benefit composition derived from iron oxidation as described above, the following non-limiting method may be used for blending the materials.

While the compositions are articles described herein are not limited by any particular method of production, the compositions may optionally be prepared through a method which includes prewetting any carbon present in the composition prior to adding to other materials or components. Indeed, it is found herein that this may be particularly important in order that the exothermic and self-steaming processes occur over a relatively long duration of time. For example, without intending to be limited by theory, it is found that, due to the water manager component's higher affinity to water, sufficient hydration of the carbon needed for increasing its catalytic activity may not be achieved. By prewetting the carbon, at least a portion of the water is reserved for increasing the catalytic activity of the carbon. The water is tightly bound by the carbon and made relatively inaccessible to the water manager component.

In accordance with this, a pre-mix may be formed by prewetting activated carbon with the water and adding in the iron, the water manager component, salt and sodium thiosulfate and any other additional components which may be used. For example, if a volatile component were to be added in it could be added to the activated carbon, added to the pre-mix formed, added to a substrate (for example, a non-woven, oxygen permeable substrate) that contains the mixture, or any combination thereof.

EXAMPLES

The following are examples of the present components, compositions, and articles. The compositions are prepared utilizing conventional processes or, preferably, the methods of production described herein. The examples are provided to illustrate the invention and are not intended to limit the scope thereof in any manner.

Example 1

A self-steaming composition for use in accordance with the present invention may be prepared as follows:

A pre-mix containing a fuel component, a water manager component, and water is prepared as follows: Activated carbon (5.58 kg) is added to a mixer, such as a Littleford Day Mixer. Water (4.28 kg) is added to the mixer, and the mixture mixes for about 10 minutes. Sponge iron (83.14 kg) is added to the mixer, and the mixture mixes for about 3 minutes. Absorbent gelling material (a polyacrylate, 7 kg) is added to the mixer, and the mixture mixes for about 12 minutes. This pre-mix is then added to a container.

Brine is prepared as follows: Water (88.3 kg) is added to a mixer. Sodium chloride (10.4 kg) and sodium thiosulfate (1.3 kg) is added to the mixer, and the mixture mixes for about 15 minutes. The resulting brine is then added to a separate container. The ratio of premix to brine can be varied to modify the amount of steam generation desired. For example, a ratio of 2:1 premix:brine, by weight, may be used.

The pre-mix and the brine solution are combined prior to packing in a final overwrap container or, alternatively, added to a substrate of an article in accordance with the present invention to form a thermal pack. If desired, one or more volatile components may be added to the composition contained within the final overwrap container, or, where applicable, the composition added to the substrate or directly to the substrate of the article. A non-limiting example includes adding the volatile component to the activated carbon, adding to the pre-mix formed, adding to a non-woven substrate that contains the composition, or combinations thereof.

Example 2

A disposable, self-steaming composition in accordance with the present invention is used to prepare an article suitable for a variety of applications, including steaming fabric or utilizing within a vaporizer for health care or other purposes. The disposable self-steaming composition article may comprise a substantially planar laminate structure having a single steam-generating heat cell or a plurality of steam-generating heat cells embedded between multiple material layers that are laminated together. The steam-generating heat cell or cells may be fixedly attached to the laminate structure. The self-steaming composition (such as, the composition in accordance with Example 1) is placed within the cell or cells and a means for allowing oxygen into the composition is provided via a permeable layer on one or more sides of the composition. A suitable heat sealable film is a polypropylene/ethylene vinyl acetate (PP/EVA) film available from Clopay Plastics of Cincinnati, Ohio as material number DH245. The laminate structure may be a nonwoven. In one non-limiting example the nonwoven may be comprised of an SMS laminate (wherein "SMS" refers to a spunbond/meltblown/spunbond laminate). The meltblown portion may be comprised of one or more layers wherein at least one meltblown layer will typically have a grammage of at least about 8 gsm. While not wishing to be bound by theory, it is believed that in self-steaming benefit compositions utilizing carbon chemistry, a meltblown layer having a grammage of at least about 8 gsm in helps prevent carbon powder from exiting the article. A suitable nonwoven is available from PGI (Polymer Group International) of Waynesboro, Va. as material number W502FWH.

In one non-limiting embodiment, a heat-sealable film is used for one side of the steam-generating heat cell and this material is attached to a porous material (for example a highly porous nonwoven) to form the steam-generating heat cell or cells. This highly porous construction also allows steam to be released from the article during use.

What is claimed is:

1. An article comprising a plurality of heat cells, wherein the heat cells comprise a composition containing: (a) a fuel component having; (b) a water manager component comprising absorbent gelling material, wherein the mean particle size distribution of the water manager component is greater than about 250 microns; (c) water wherein the water is physically or chemically held to the water manager; and (d) pre-wetted carbon; wherein the composition is exothermic upon contact with oxygen and is self-steaming upon contact with oxygen; and wherein the article generates at least $2 \times 10^{-5}$ g/minute of steam.

2. The article according to claim 1 wherein the fuel component comprises a material selected from the group consisting of metals, metal salts, carbon, and mixtures thereof.

3. The article according to claim 1 wherein the mean particle size distribution of the water manager component is at least about 400 microns.

4. The article according to claim 1 wherein the fuel component comprises iron, a metal salt, and pre-wetted activated carbon.

5. The article according to claim 4 wherein the mean particle size distribution of the fuel component is at least about 100 microns.

6. The article according to claim 5 comprising from about 0.1% to about 30% of the water manager component, by weight of the composition.

7. The article according to claim 6 comprising from about 30% to about 95% of the iron, from about 0.5% to about 10% of the metal salt, from about 0.5% to about 25% of the pre-wetted activated carbon, and from about 1% to about 60% of the water, all by weight of the composition.

8. The article composition according to claim 7 wherein the wherein the mean particle size distribution of the water manager component is from about 400 microns to about 800 microns and wherein the wherein the mean particle size distribution of the fuel component is from about 100 microns to about 300 microns.

9. An article comprising a plurality of heat cells, wherein the heat cells comprise a composition containing: (a) a fuel component; (b) a water manager component comprising absorbent gelling material; (c) water wherein the water is physically or chemically held to the water manager, and (d) pre-wetted carbon; and wherein the ratio of the water manager component to the water is from about 0.001:1 to about 0.2:1, by weight, wherein the composition is exothermic upon contact with oxygen and is self-steaming upon contact with oxygen; and wherein the article generates at least $2 \times 10^{-5}$ g/minute of steam.

10. The article according to claim 9 wherein the ratio of the water manager component to the water is from about 0.01:1 to about 0.17:1, by weight.

11. The article according to claim 10 wherein the fuel component comprises a material selected from the group consisting of metals, metal salts, carbon, and mixtures thereof.

12. The article according to claim 9 wherein the fuel component comprises iron, a metal salt, and pre-wetted activated carbon.

13. The article according to claim 12 comprising from about 0.1% to about 30% of the water manager component, by weight of the composition.

14. The article according to claim 13 comprising from about 30% to about 95% of the iron, from about 0.5% to about 10% of the metal salt, from about 0.5% to about 25% of the pre-wetted activated carbon, all by weight of the composition.

15. The article according to claim 14 wherein the ratio of the water manager component to the water is from about 0.05:1 to about 0.12:1, by weight.

16. An article comprising a plurality of heat cells, wherein the heat cells comprise a composition containing: (a) a fuel component comprising sponge iron; (b) a water manager component comprising absorbent gelling material; (c) water wherein the water is physically or chemically held to the water manager, and (d) pre-wetted carbon; and wherein the composition is exothermic upon contact with oxygen and is self-steaming upon contact with oxygen; and wherein the article generates at least $2 \times 10^{-5}$ g/minute of steam.

17. The article according to claim 16 wherein the fuel component further comprises a material selected from the group consisting of metal salts, carbon, and mixtures thereof.

18. The article according to claim 16 wherein the fuel component comprises a metal salt and pre-wetted activated carbon.

19. The article according to claim 18 comprising from about 0.1% to about 30% of the water manager component, by weight of the composition.

20. The article according to claim 19 comprising from about 30% to about 95% of the sponge iron, from about 0.5% to about 10% of the metal salt, from about 0.5% to about 25% of the pre-wetted activated carbon, and from about 1% to about 60% of the water, all by weight of the composition.

21. The article according to claim 1 comprising an enclosure which contains the composition, wherein the enclosure is impermeable to air.

22. The article according to claim 9 comprising an enclosure which contains the composition, wherein the enclosure is impermeable to air.

23. The article according to claim 16 comprising an enclosure which contains the composition, wherein the enclosure is impermeable to air.

24. The article according to claim 1 comprising: (a) a thermal pack, wherein the thermal pack comprises a material which is permeable to air.

25. The article according to claim 24, wherein the thermal pack further comprises a material which is impermeable to air.

26. The article according to claim 25 wherein the material which is permeable to air is selected from the group consisting of woven fabrics, knit fabrics, nonwovens, and combinations thereof and wherein the material which is impermeable to air is selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

27. The article according to claim 9 comprising: (a) a thermal pack, wherein the thermal pack comprises a material which is permeable to air.

28. The article according to claim 27, wherein the thermal pack further comprises a material which is impermeable to air.

29. The article according to claim 28 wherein the material which is permeable to air is selected from the group consisting of woven fabrics, knit fabrics, nonwovens, and combinations thereof and wherein the material which is impermeable to air is selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

30. The article according to claim 16 comprising: (a) a thermal pack, wherein the thermal pack comprises a material which is permeable to air.

31. The article according to claim 30 which is a vaporizer.

32. An article comprising a plurality of heat cells, wherein the heat cells comprise a composition containing: (a) a fuel component; (b) a water manager component comprising absorbent gelling material; (c) water wherein the water is physically or chemically held to the absorbent gelling material; and (d) pre-wetted carbon, and (e) a material having an oxygen permeability of at least about 10 ft.sup.3/cm wherein the article is self-steaming upon contact with oxygen; and wherein the article generates at least $2 \times 10^{-5}$ g/minute of steam.

33. The article according to claim 32 wherein the material has an oxygen permeability of at least about 20 ft.sup.3/cm.

34. The article according to claim 33 wherein the material has an oxygen permeability of from about 20 ft.sup.3/min to about 150 ft.sup.3/min.

35. The article according to claim 34 wherein the material is selected from the group consisting of woven fabrics, knit fabrics, nonwovens, and combinations thereof and further including a second material impermeable to air selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

* * * * *